(12) United States Patent
Hu

(10) Patent No.: US 9,084,846 B2
(45) Date of Patent: Jul. 21, 2015

(54) COMBINATION SUCTION REGULATOR FOR MEDICAL USE

(75) Inventor: Yuegang Hu, Shanghai (CN)

(73) Assignee: GENTEC (SHANGHAI) CORPORATION, Shanghai (CN)

(\*) Notice: Subject to any disclaimer, the term of this patent is extended or adjusted under 35 U.S.C. 154(b) by 928 days.

(21) Appl. No.: 12/132,603

(22) Filed: Jun. 3, 2008

(65) Prior Publication Data

US 2009/0082741 A1 Mar. 26, 2009

(30) Foreign Application Priority Data

Sep. 21, 2007 (CN) ...................... 2007 2 0074917 U

(51) Int. Cl.
*A61M 1/00* (2006.01)

(52) U.S. Cl.
CPC .................................. *A61M 1/0037* (2013.01)

(58) Field of Classification Search
CPC ...................................... A61M 1/0031–1/0037
USPC ......... 604/311, 313, 317, 319, 320, 329, 331; 601/6, 313; 73/861.77; 137/557, 137/624.11; 324/207.25; 123/41.1, 41.29, 123/41.31; 600/311, 345, 347
See application file for complete search history.

(56) References Cited

U.S. PATENT DOCUMENTS

| | | | | |
|---|---|---|---|---|
| 3,794,026 | A * | 2/1974 | Jacobs | 128/200.13 |
| 7,438,705 | B2 * | 10/2008 | Karpowicz et al. | 604/313 |
| 2009/0192367 | A1 * | 7/2009 | Braig et al. | 600/311 |

\* cited by examiner

*Primary Examiner* — Philip R Wiest
*Assistant Examiner* — Benjamin Klein

(57) ABSTRACT

A combination suction regulator for medical use which comprises a cover, a vacuum gauge, a regulating module, an integrated flow channel module having a plurality of board surface flow channels, an intermittent timer module, a mode select switch, a vacuum relief and an air buffer. The air buffer is disposed inside the cover and integrally formed as a whole with the integrated flow channel module. A flow channel board and a bottom board coupled with each other to form the integrated flow channel module. The intermittent timer module comprises a diaphragm piston disposed on one side and the change valve disposed on another side of the middle part of the front side of the flow channel board.

6 Claims, 15 Drawing Sheets

COMBINATION SUCTION REGULATOR FOR MEDICAL USE

BACKGROUND OF THE INVENTION

The present invention relates to a vacuum regulating means for medical use and more particularly pertains to a combination suction regulator for medical use which is mainly used for clinical vacuum suction.

A suction regulator is a regulation means for controlling the vacuum and flow of the vacuum source from a vacuum terminal of a vacuum supply system. It forms a suction system with a liquid collection bottle for clinical liquid suction. See FIG. 1 for the construction of the system.

There are two types of suction regulators now available in the marketplace:

(a) Normal suction regulators: the operation mode is a continuous suction mode which can be further divided into two operation modes, namely vacuum regulable operation mode and full direct operation mode. They can satisfy the needs of general clinical vacuum suction (respiratory tract and mouth cavity).

(b) Intermittent suction regulators: the operation modes are intermittent suction mode and continuous suction mode. The continuous suction mode is the same as normal regulable operation mode. When the intermittent suction mode is selected, under the effect of an intermittent timer, the suction operation is switched on and off according to predetermined time intervals to allow an intermittent suction mode.

BRIEF SUMMARY OF THE INVENTION

The object of the present invention is to resolve the problem that the use of continuous suction regulators may be discontinued by blockage of the suction mouth by human soft tissues or by other articles in special situations or conditions.

To attain the above object, a suction regulator according to the present invention generally comprises a cover (1), a vacuum gauge (2), a regulating module (3), a mode select switch (4), an intermittent timer (5), an integrated flow channel module (6), an air buffer (7) and a vacuum relief (8), wherein (see FIGS. 2, 3):

A. the air buffer (7) is disposed inside the cover (1) and integrally formed as a whole with the integrated flow channel module (6), two air holes (7a, 7b) are disposed on a right and a left side of a bottom part of the air buffer (7) for connecting board surface flow channels (L1-L4) of the integrated flow channel module (6) that are susceptible to interference (see FIG. 4);

B. a flow channel board (6-1) and a bottom board (6-2) are coupled with each other to form the integrated flow channel module (6); there is a probe/adapter port (P1) for connecting with an input vacuum source and three timer regulating needle valves (T0,T1,T2) for communicating with corresponding board surface flow channels (L1-L4) to adjust time of the intermittent timer (5) at a middle part of a back side of the integrated flow channel module (6); at a front side of the integrated flow channel module (6), a pole (6A) at an upper end thereof for installing the mode select switch (4), four to six board surface flow channel connection holes Sf1-Sf6 for communicating with the board surface flow channels (L1-L4), and a sleeve seat (6B) for the vacuum gauge (2) are provided. At a middle part of a front side of the flow channel board (6-1), a metal pole (6C), a timer channel hole (6E) and a valve seat (5-2-1) of a change valve (5-2) are disposed for connecting to the intermittent timer (5). At a lower part of the front side of the flow channel board (6-1), another sleeve seat (6D) is disposed for installing the regulating module (3). At a bottom part of the flow channel board (6-1), there is a fitting port (P2) which forms an outlet of the suction regulator (see FIG. 4).

C. the intermittent timer (5) comprises a diaphragm piston (5-1) and the change valve (5-2) disposed on a middle part of a front side of the integrated flow channel module (6); the diaphragm piston (5-1) comprises mainly a piston body (5-1-1), a diaphragm (5-1-2), a return spring (5-1-3) and a piston rod (5-1-4); the change valve (5-2) comprises mainly a connecting rod (5-2-5), a crank (5-2-4) and a torsion spring (5-2-3); a valve plate (5-2-2) and the valve seat (5-2-1) are assembled on the integrated flow channel module (6) (see FIG. 7).

In an embodiment, the flow channel board (6-1) has six board surface flow channel connection holes Sf1-Sf6 at an upper end of the front side thereof, and six corresponding board surface flow channel connection holes Sb1-Sb6 on a back side thereof; the six board surface flow channel connection holes Sf1-Sf6 and the mode select switch flow channels S1, S2 on the mode select switch (4) form a mode selector (see FIGS. 5, 6).

The valve seat (5-2-1) in the middle part of the front side of the flow channel board (6-1) has six valve channel holes Qf1-Qf6 and the valve plate (5-2-2) has three change valve flow channels C1,C2,C3. There are another six valve channel holes Qb1-Qb6 on the back side of the flow channel board (6-1) corresponding to the six valve channel holes Qf1-Qf8; five of the valve channel holes Qb1, Qb3-Qb6 communicate with the corresponding board surface flow channels (L1-L4) on the back side of the flow channel board (6-1) (see FIGS. 5, 7).

The middle part of the front side of the flow channel board (6-1) has two holes Pf1, Pf2 which communicate with the air buffer (7) (see FIG. 4).

The holes J1,J2,J3 on the flow channel board (6-1) correspond to the timer regulating needle valves T0,T1,T2 (see FIGS. 5,6).

In comparison with the conventional suction regulators for medical use, the whole construction of the present invention based on the above technical solutions is more compact and aesthetically pleasing as the air buffer (7) is disposed inside the instrument. Moreover, through combination of the special surface board flow channels (L1-L4) on the back side of the flow channel board (6-1) which forms a part of the integrated flow channel module (6), the "instant off" or "instant on" suction mode can be obtained by changing only the valve plate (5-2-2) (see FIG. 7). Furthermore, the setup of the intermittent timer (5) is changed from inside to outside, resulting in very convenient time setting.

DETAILED DESCRIPTION OF THE INVENTION

Figure 1:
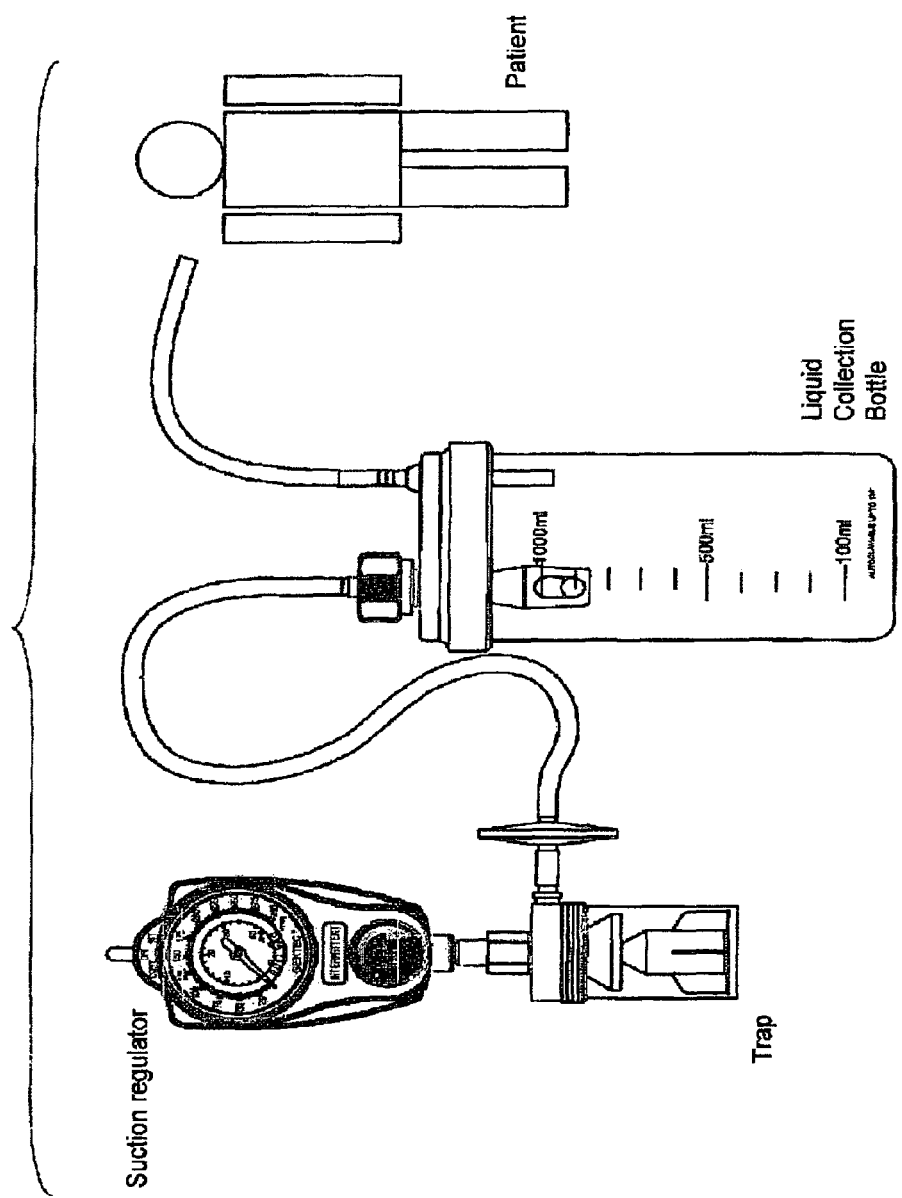
FIG. 1 illustrates the construction of the suction system.
Figure 2:
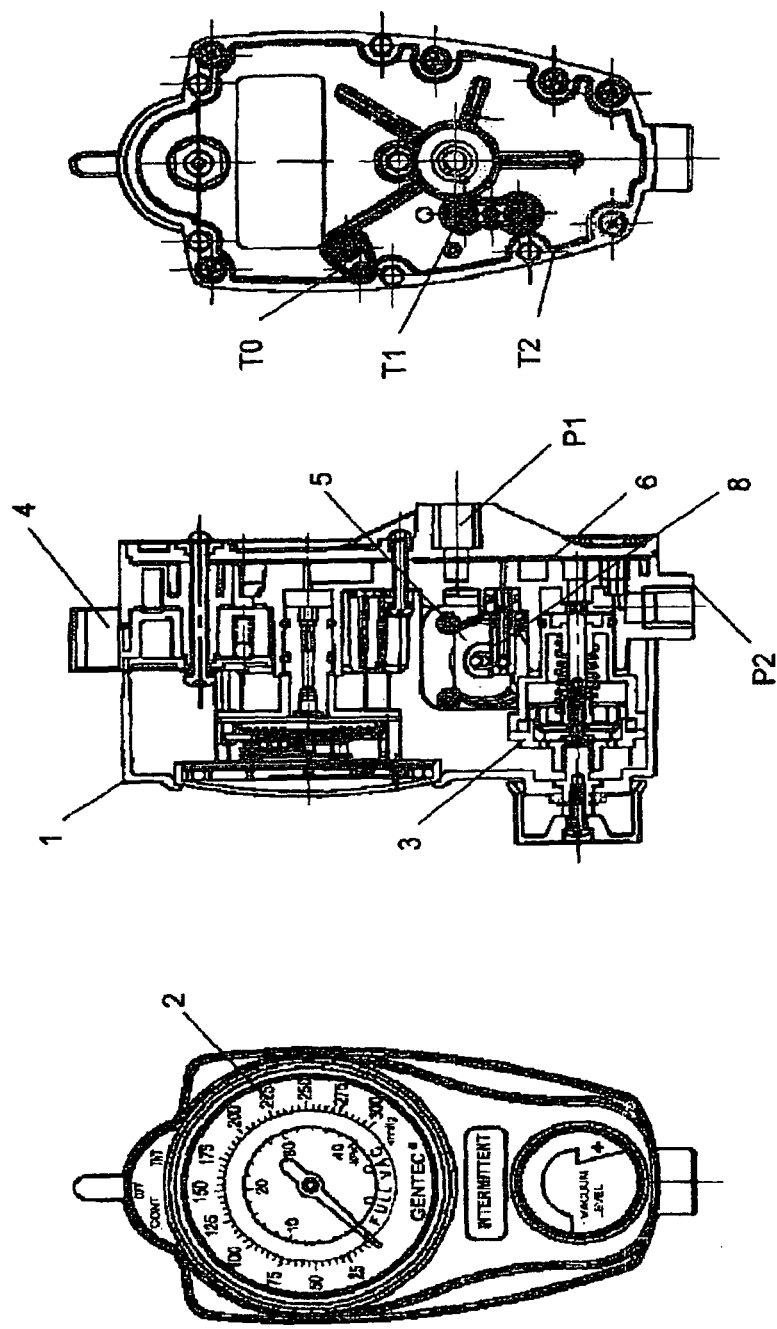
FIG. 2 illustrates assembled views of the suction regulator.
Figure 3:
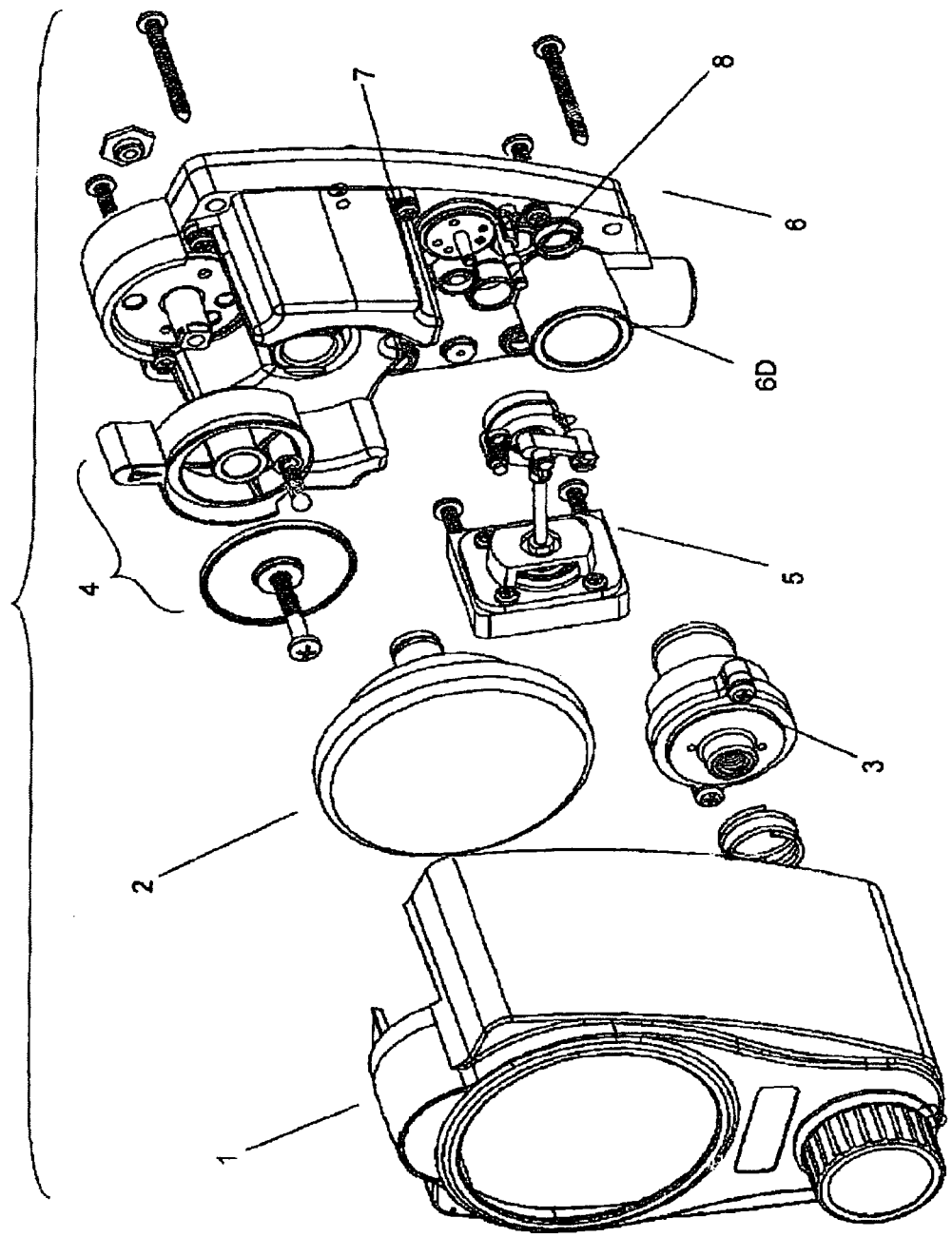
FIG. 3 is an exploded view of the suction regulator.
Figure 4:
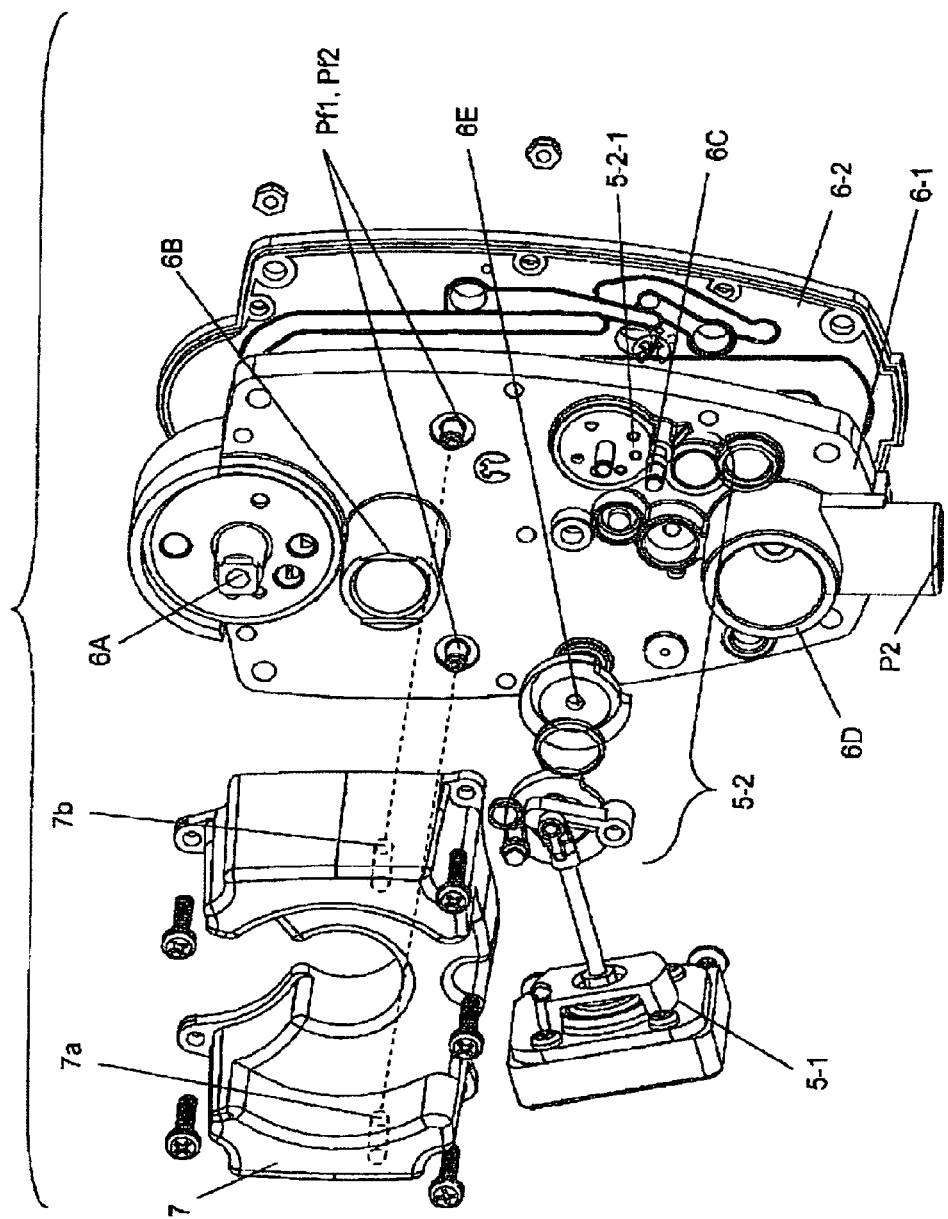
FIG. 4 is an exploded view of the integrated flow channel module, the air buffer and the intermittent timer.

The present invention is further described in detail with the following embodiment and the accompanying drawings.

As shown in the drawings, the present invention is an inventive improvement to conventional devices having the same function. The improved technical proposal is detailed in the following. The combination suction regulator for medical use of the present invention generally comprises a cover (1), a vacuum gauge (2), a regulating module (3), an integrated flow channel module (6), an intermittent timer (5), and an air buffer (7), wherein:

A. The air buffer (7) is disposed inside the cover (1) and integrally formed as a whole with the integrated flow channel module (6). The air buffer (7) has two air holes (7a, 7b) disposed at a bottom part thereof for communicating with the board surface flow channels (L1-L4) of the integrated flow channel module (6) that are susceptible to interference.

B. A flow channel board (6-1) and a bottom board (6-2) coupled with each other to form the integrated flow channel module (6). The flow channel bottom board (6-2) has a probe/adapter port (P1) at a middle part thereof for connecting with an input vacuum source, and three timer regulating needle valves (T0, T1, T2) on a bottom board surface thereof for communicating with corresponding board surface flow channels (L1-L4). The flow channel board (6-1) has a pole (6A) at an upper end thereof for installing a mode select switch (4) and four to six board surface flow channel connection holes Sf1-Sf6 for communicating with the board surface flow channels (L1-L4) on the back side of the flow channel board (6-1) and a sleeve seat (6B) for the vacuum gauge (2). In a middle part of a front side of the flow channel board (6-1), a metal pole (6C), a timer channel hole (6E) and a valve seat (5-2-1) are disposed, all of which are connected to the intermittent timer (5). In a lower part of the front side of the flow channel board (6-1), a sleeve seat (6D) is disposed for installing the regulating module (3). In the sleeve seat (6D), there are mouths for communicating with the board surface flow channels (L1-L4) on the back side of the flow channel board (6-1). There is a fitting port (P2) which forms an outlet of the suction regulator at a bottom part of the flow channel board (6-1).

C. The intermittent timer (5) comprises a diaphragm piston (5-1) and the change valve (5-2) disposed on the middle part of the front side of the integrated flow channel module (6); the diaphragm piston (5-1) comprises mainly a piston body (5-1-1), a diaphragm (5-1-2), a return spring (5-1-3) and a piston rod (5-1-4); the change valve (5-2) comprises mainly a connecting rod (5-2-5), a crank (5-2-4) and a torsion spring (5-2-3 and a valve plate (5-2-2) and a valve seat (5-2-1); the diaphragm piston (5-1) connects to the change valve (5-2) through the piston rod (5-1-4).

When an "instant off" combination suction regulator is in the intermittent mode, a main gas path of the change valve (5-2) is blocked and a controlling gas path of the change valve (5-2) is open, the vacuum source can communicate with the diaphragm piston (5-1) through the change valve (5-2) and the regulation of the first timer regulating needle valve (T0) and the air buffer (7), the diaphragm piston (5-1) overcomes the force of the return spring (5-1-3) inside the diaphragm piston (5-1) and gradually pulls the piston rod (5-1-4) to actuate the connecting rod (5-2-5) of the change valve (5-2) to rotate around the metal pole (6C). When the connecting rod (5-2-5) rotates to a critical position, the crank (5-2-4) loses its stability under the action of the torsion spring (5-2-3) of the change valve (5-2), and the torsion spring (5-2-3) acts on the crank (5-2-4) to actuate the valve plate (5-2-2) of the change valve (5-2) to rotate rapidly, thereby forcing change valve flow channels (C1, C2, C3) of the change valve (5-2) to be shifted and the directions of the main gas path and the controlling gas path to be changed. The blocked main gas path is unblocked; the controlling gas path is blocked and the vacuum status in the diaphragm piston (5-1) is relieved. Under the action of the return spring (5-1-3), the diaphragm piston (5-1) and the connecting rod (5-2-5) and other components start to return to their original positions. When the connecting rod (5-2-5) goes back to another critical position, the crank (5-2-4) again loses its stability, and the crank (5-2-4) actuates the valve plate (5-2-2) of the change valve (5-2) to rotate rapidly to the original position under the effect of the torsion spring (5-2-3). The change valve flow channels (C1, C2, C3) again shift back to their original positions and a cycle is completed. To repeat the above cycle, the vacuum source communicates again with the diaphragm piston (5-1) of the intermittent timer (5). In the other way round, the "instant on" combination suction regulator is first on and then off while the valve plate is replaced.

The flow channel board (6-1) has four to six board surface flow channel connection holes (Sf1-Sf6) at the upper end of the front side thereof, and four to six corresponding board surface flow channel connection holes (Sb1-Sb6) on the back side thereof. The four to six board surface flow channel connection holes (Sf1-Sf6) form a mode selector with mode select switch flow channels (S1, S2) of the mode select switch (4) (see FIG. 5, 6).

Figure 7:
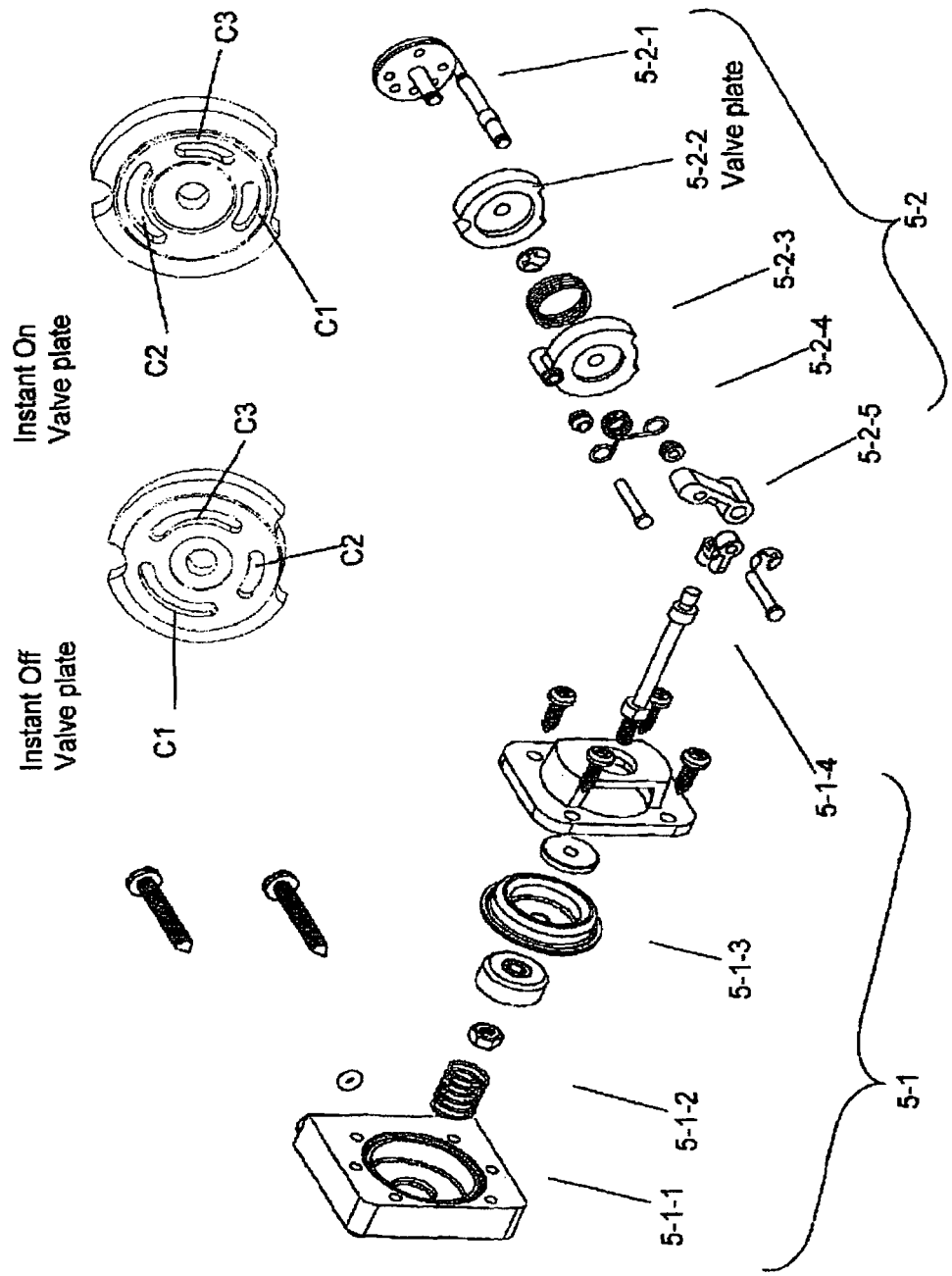
FIG. 7 is an exploded view of the intermittent timer.

The valve seat (5-2-1) of the change valve (5-2) in the middle part of the front side of the flow channel board (6-1) has six valve channel holes (Qf1-Qf6) and six corresponding valve channel holes (Qb1-Qb6) on the back side thereof. The valve plate (5-2-2) of the change valve (5-2) has the change valve flow channels (C1-C3) which form a slide valve with the six valve channel holes (Qf1-Qf6) on the valve seat (5-2-1). There are two types of valve plate (5-2-2), namely an "instant off" valve plate and an "instant on" valve plate (see FIG. 7).

The middle part of the front side of the flow channel board (6-1) has two holes (Pf1, Pf2) which communicate with the two air holes (7a, 7b) at the bottom part of the air buffer (7).

Figure 5:
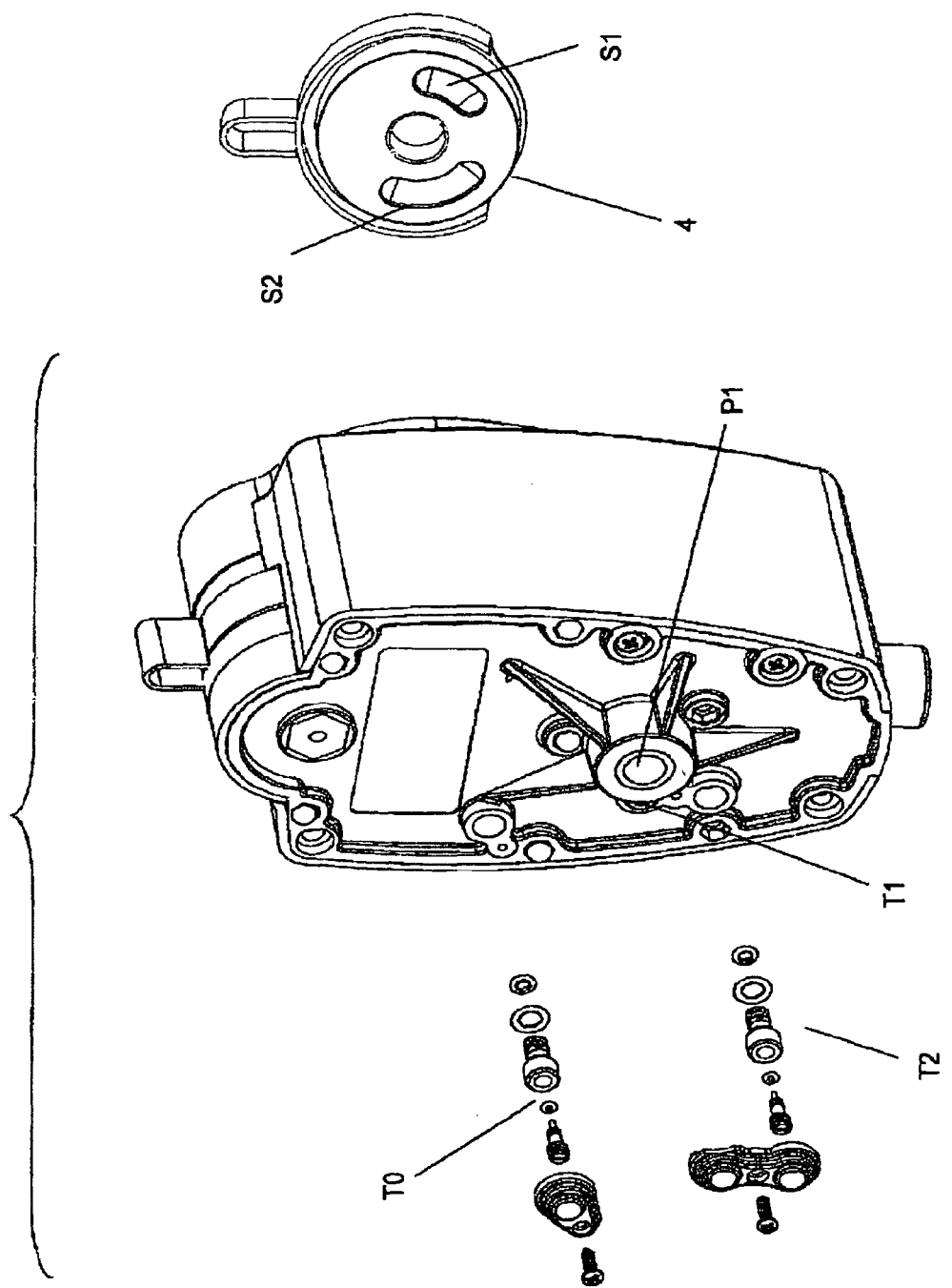
FIG. 5 shows a back view of the suction regulator and the mode select switch flow channels of the mode select switch.

The holes J1, J2, J3 on the flow channel board (6-1) correspond to the first to third timer regulating needle valves (T0, T1, T2) respectively (see FIG. 5,6). The first and the third timer regulating needle valves (T0, T2) are used only for "instant off".

The present invention is described in view of the above embodiment, but those skilled in the art should understand that the above embodiment is only used for describing the present invention. The present invention can be implemented in accordance with other embodiments by making different variations and amendments and is not limited by the above embodiment. Any other variations or changes, whether in substance or in principle, not deviated from the spirit of the present invention, should fall within the scope of protection of the present invention.

Operation Principle

A) Off Operation Mode

When the mode select switch (4) is switched to the middle position (OFF), vacuum source communicates with the board surface flow channel L1 from the probe/adapter port (P1) to reach the board surface flow channel connection hole Sb1 and then the board surface flow channel connection hole Sf1 at the front side of flow channel board (6-1). Since the board surface flow channel connection hole Sf1 is blocked by the mode select switch (4), communication of the vacuum source is cut and the system is therefore closed. The operation mode is off and the suction regulator does not work.

B) Continuous Operation Mode

Figure 6:
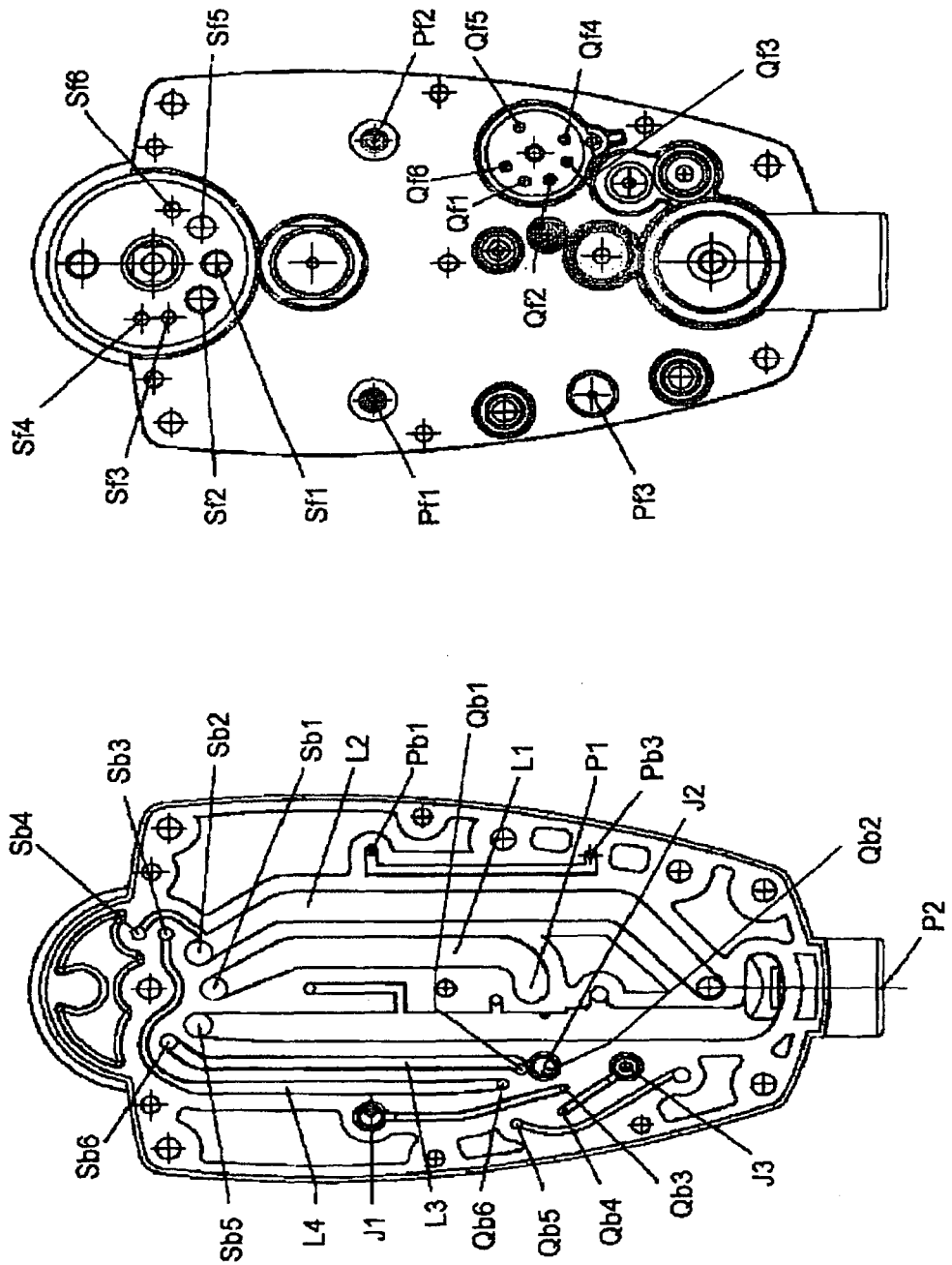
FIG. 6 illustrates the flow channel board.
Figure 8:
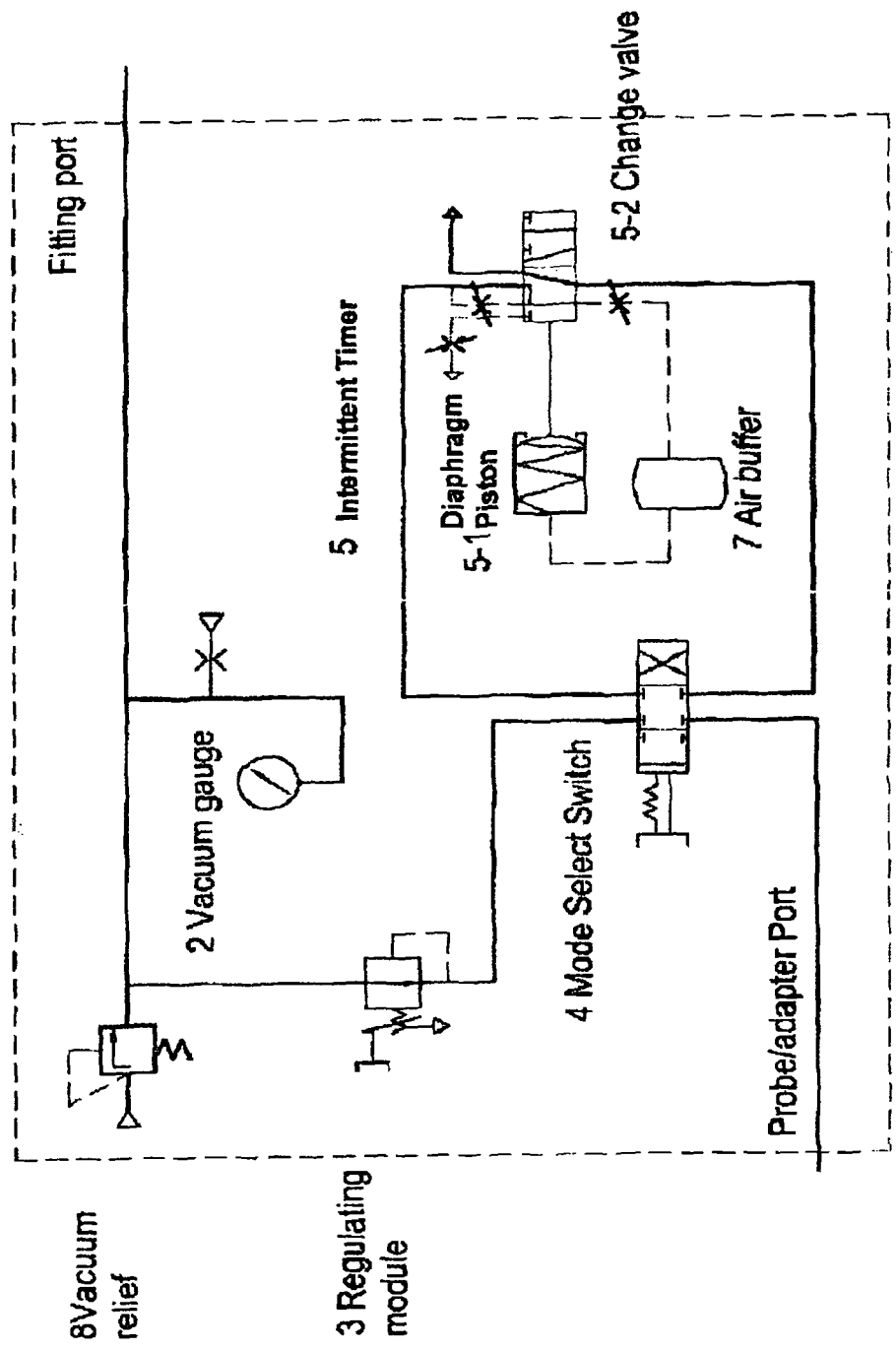
FIG. 8 is a diagram of the "instant off" combination suction regulator.
Figure 9:
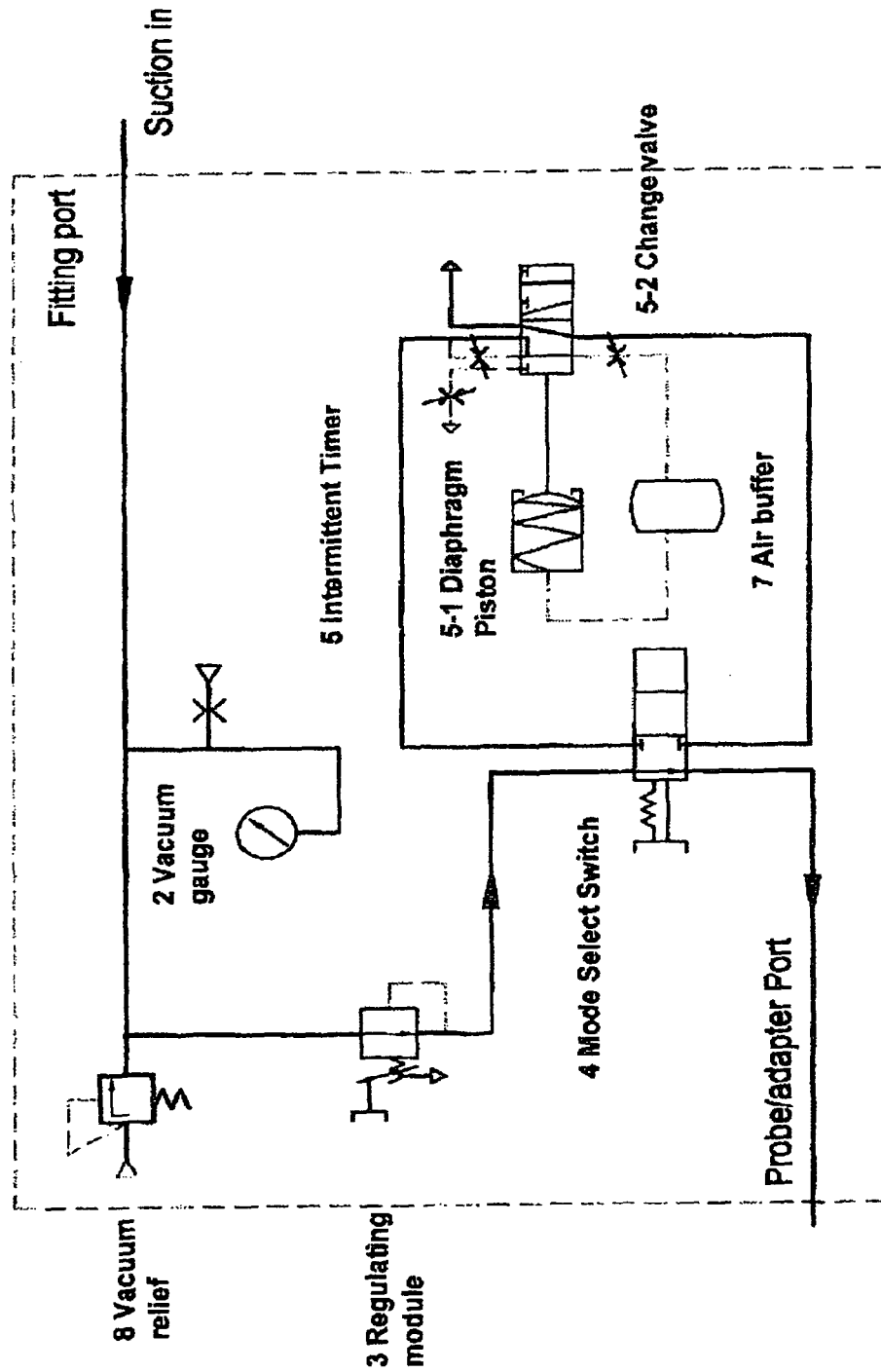
FIG. 9 is a process flow diagram of the continuous mode of the "Instant off" combination suction regulator.

When the mode select switch (4) is switched to the left position (CONT), the operation mode is continuous. Vacuum source communicates with the integrated flow channel module (6) from the probe/adapter port (P1). The mode select switch flow channel S1 of the mode select switch (4) enables the board surface flow channel connection hole Sf1 to communicate with the board surface flow channel connection Sf2, and the vacuum source communicates with the board surface flow channel connection hole Sb2 and then with the regulating module (3) through the board surface flow channel L2. Vacuum power is then output from the fitting port (P2) after the adjustment of the vacuum level to allow continuous suction operation. At this time, the suction regulator is in the continuous operation mode (see FIGS. 6, 8, 9).

C) Intermittent Operation Mode of "Instant Off"

Figure 10:
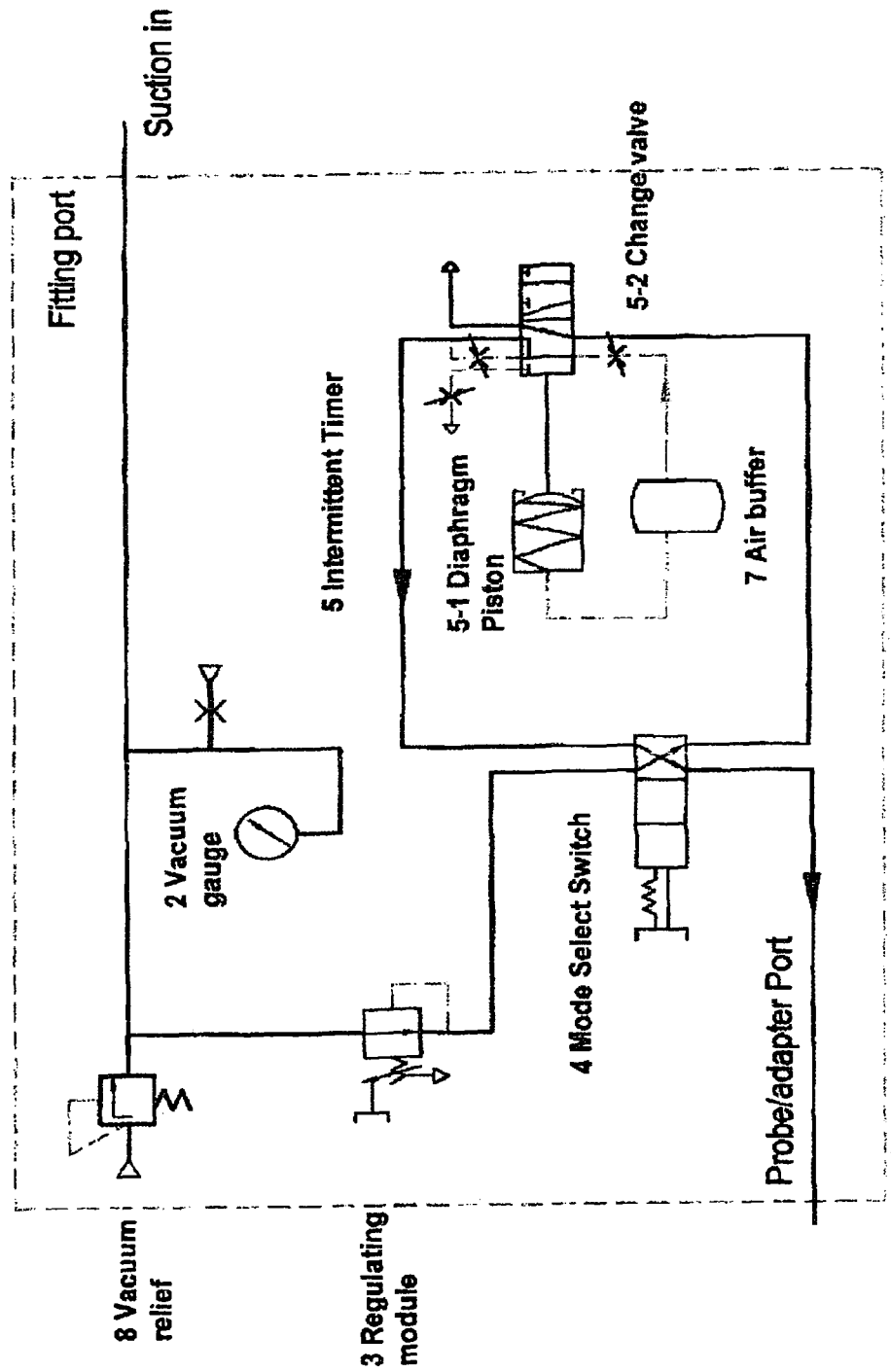
FIG. 10 is a process flow diagram of the close situation of the intermittent mode of the "instant off" combination suction regulator.
Figure 11:
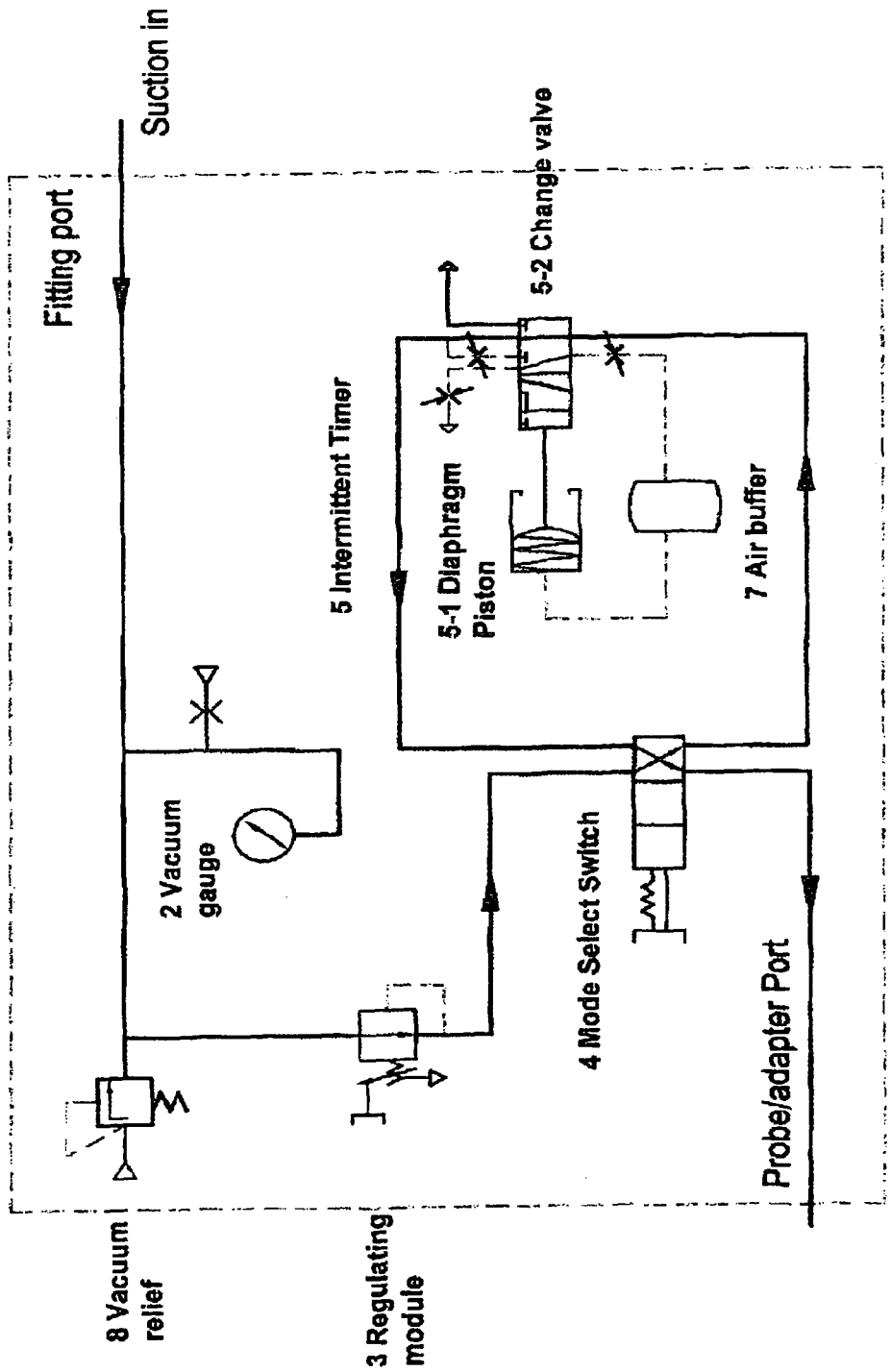
FIG. 11 is a diagram of the flow path of the open situation of the "instant off" combination suction regulator.
Figure 12:
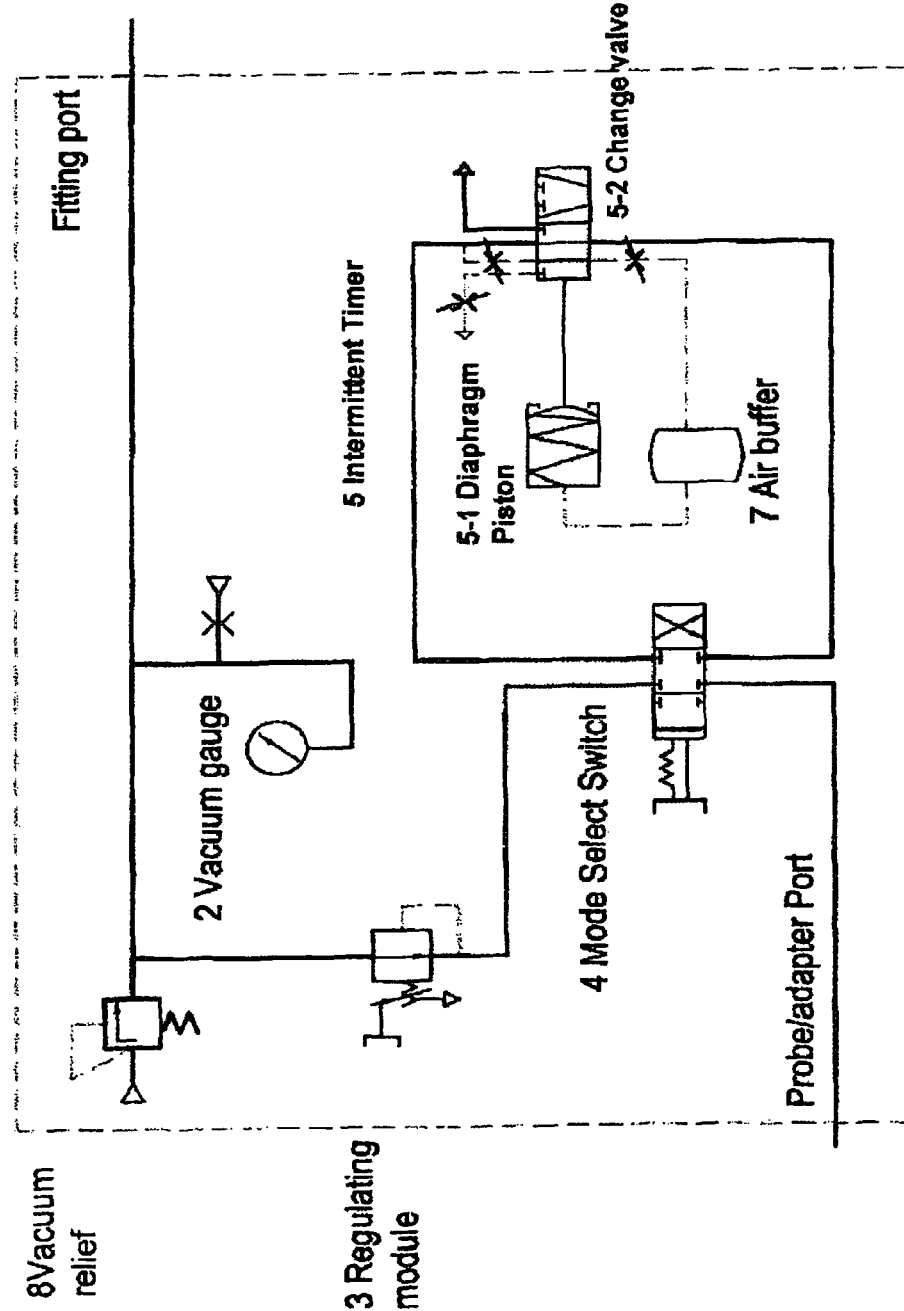
FIG. 12 is a diagram of the "instant on" combination suction regulator.
Figure 13:
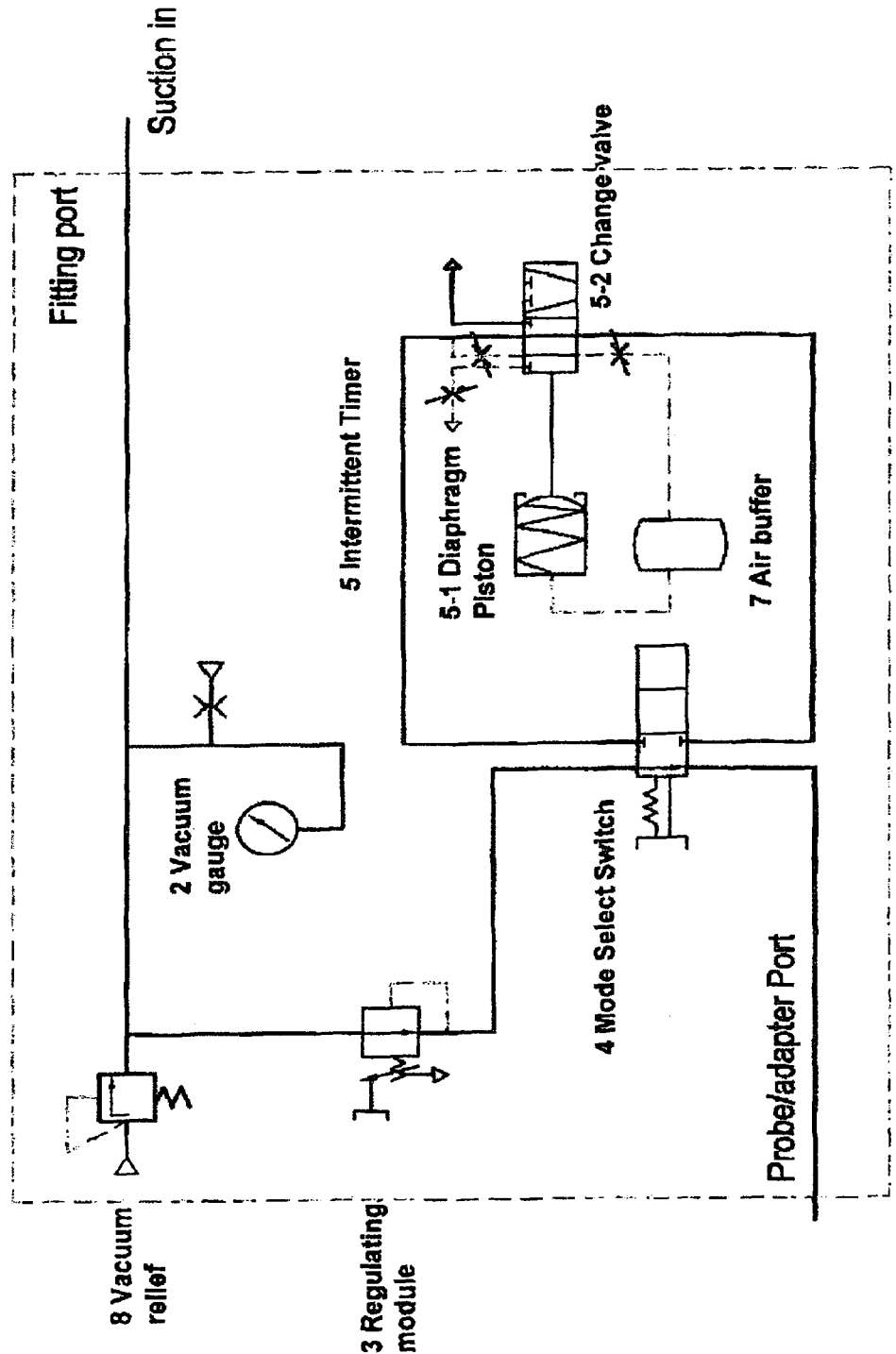
FIG. 13 is a process flow diagram of the continuous mode of the "instant on" combination suction regulator.
Figure 14:
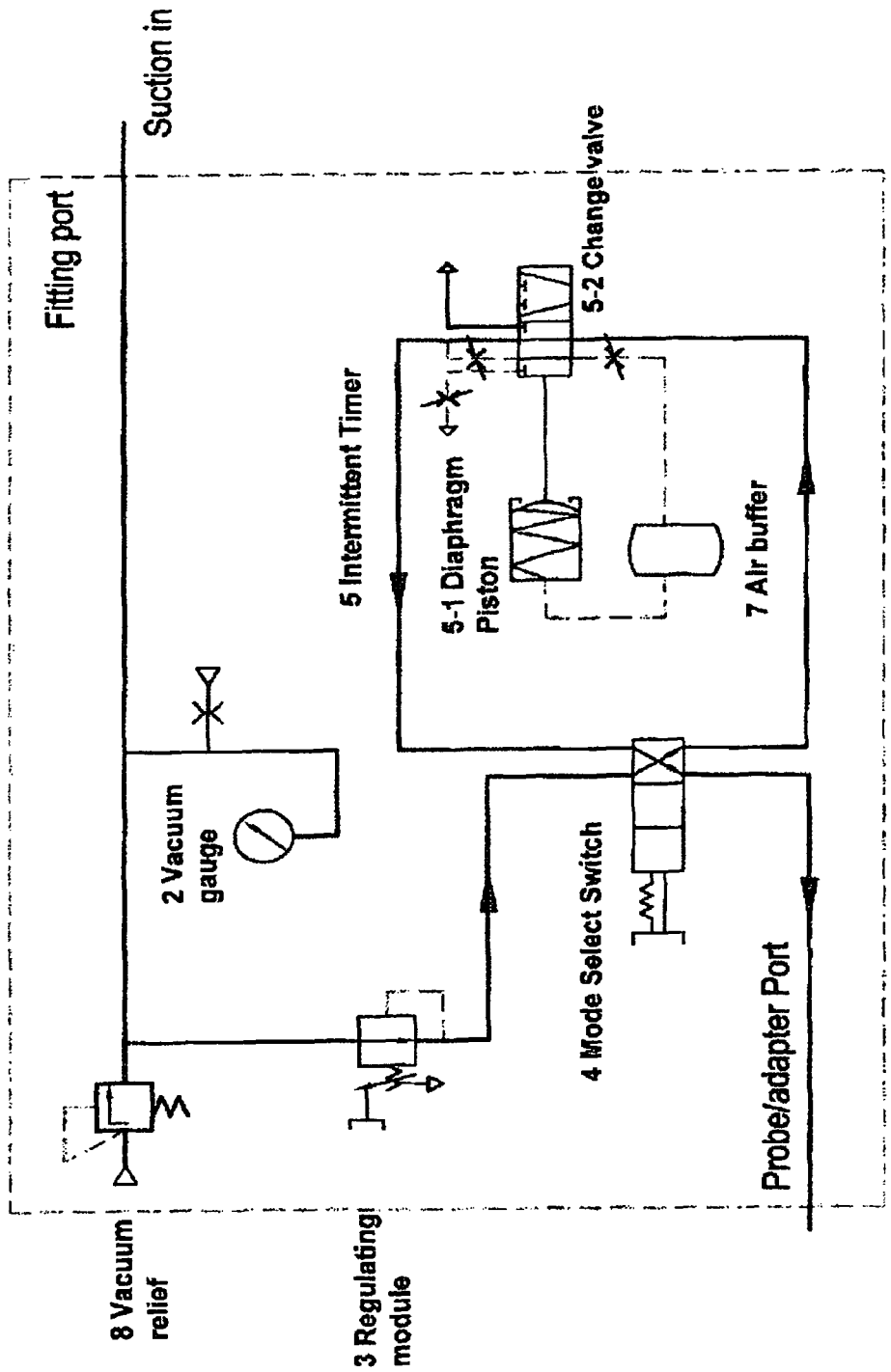
FIG. 14 is a process flow diagram of the open situation of the intermittent mode of the "instant on" combination suction regulator.
Figure 15:
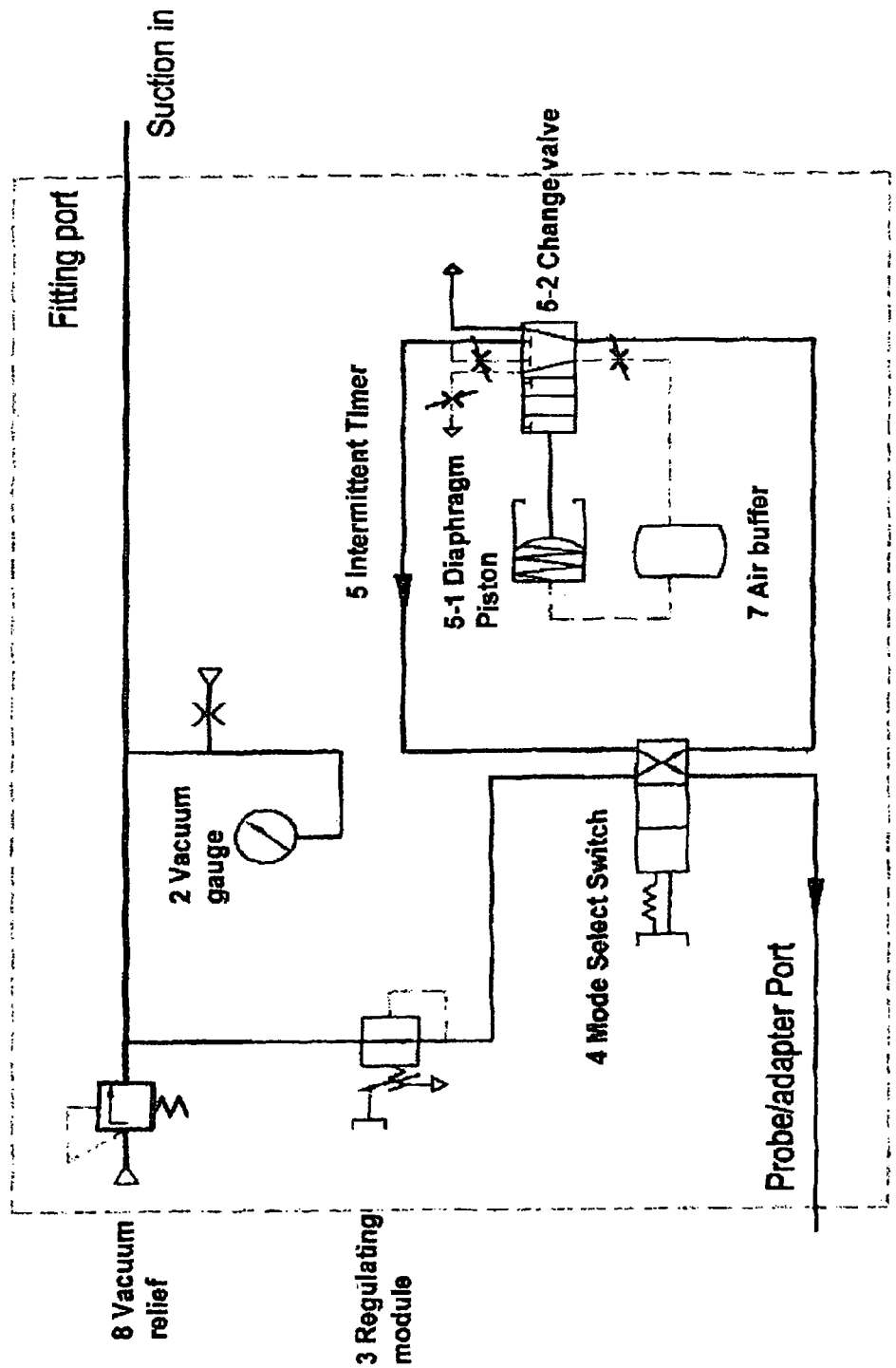
FIG. 15 is a process flow diagram of the close situation of the intermittent mode of the "instant on" combination suction regulator.

When the mode select switch (4) is turned to the right position (INT), the operation mode is intermittent:

1) At the beginning, the suction regulator is off (in case of "instant on" operation, the suction regulator is on). The vacuum source communicates with the board surface flow channel L1 of the integrated flow channel module (6) from the probe/adapter port (P1) and the vacuum power reaches the change valve (5-2) through the board surface flow channel connection hole Sf1, the mode select switch flow channel S2, the board surface flow channel connection hole Sf6 and the board surface flow channel L3 in the integrated flow channel module (6) and the mode select switch (4). At this time, the main gas path of the change valve (5-2) is closed and the suction regulator is stopped. The controlling gas path of the change valve (5-2) is opened (see FIG. 10, the solid line is the main gas path, the dotted line is the controlling gas path).

2) The vacuum source communicates with the diaphragm piston (5-1) of the intermittent timer (5) through the valve channel hole Qf1, the change valve flow channel C3, the valve channel hole Qf3, the air buffer (7) and by adjustment of the first timer regulating needle valve T0. Under the effect of vacuum, the diaphragm piston (5-1) pulls the connecting rod (5-2-5). When the connecting rod (5-2-5) reaches a critical position, the crank (5-2-4) loses its stability under the action of the torsion spring (5-2-3), and the crank (5-2-4) actuates the valve plate (5-2-2) to rotate rapidly and thereby forcing the change valve (5-2) to change its status. The directions of the paths are changed wherein the main gas path of the change valve (5-2) becomes open and the controlling gas path becomes close (see FIG. 10).

3) The vacuum power enters the regulating module (3) through the mode select switch flow channel S1 of the mode select switch (4). The vacuum power output at the fitting port (P2) can be set to the desired value by adjusting a knob of the regulating module (3). The suction operation then starts.

At the same time, after the controlling gas path is closed, the vacuum source communicating with the diaphragm piston (5-1) is cut off and under the effect of the return spring (5-1-3), the vacuum power begins to be relieved. The speed of vacuum relief is adjusted by the third timer regulating needle valve (T2), and the intermittent timer (5) slowly returns to its original position. When the connecting rod (5-2-5) returns to a critical position, the crank (5-2-4) loses its stability again under the action of the torsion spring (5-2-3), and the crank (5-2-4) actuates the valve plate (5-2-2) to rotate rapidly and thereby forcing the change valve (5-2) to change its status. The change valve flow channels (C1-C3) return to their original status and a cycle is completed.

The detailed operation process of the above operation principle is as follows:

A) When the mode select switch (4) is switched to the right position, the mode select switch flow channel S2 of the mode select switch (4) enables the board surface flow channel connection hole Sf1 to communicate with the board surface flow channel connection hole Sf6, and the vacuum power enters the valve channel hole Qb1 of the change valve (5-2) through the board surface flow channel L3 from the board surface flow channel connection hole S136 and then reaches the valve channel hole Qf1 at the front side. The main gas path is blocked by the valve plate (5-2-2) of the change valve (5-2) and is closed. At the same time, the change valve flow channel C3 of the valve plate (5-2-2) enables the valve channel holes Qf1, Qf2 and Qf3 to communicate with each other, and the vacuum power is sequentially sucked into the valve channel hole Qb3, the first timer regulating needle valve T0 and the hole Pf2, and by effectively making use of the air buffer (7), the vacuum power jumps over the flow channel board (6-1) and enters the hole Pf1, a hole Pb1 corresponding to the hole Pf1, a hole Pb3 communicating with the hole Pb1 and a hole Pf3 corresponding to the hole Pb3 and to the diaphragm piston (5-1) so as to begin the operation of the timer in order to pull the connecting rod (5-2-5) of the change valve (5-2).

B) When the connecting rod (5-2-5) moves to the critical position, the crank (5-2-4) loses its stability under the action of the torsion spring (5-2-3), and the crank (5-2-4) actuates the valve plate (5-2-2) to rotate rapidly and thereby forcing the change valve (5-2) to change its status. The directions of the change valve flow channels are changed. The change valve flow channel C3 of the valve plate (5-2-2) of the change valve (5-2) enables the valve channel holes Qf6, Qf1 and Qf2 to communicate with each other, and the vacuum power reaches the board surface flow channel connection hole Sf3 through the valve channel hole Qb6, the board surface flow channel L4 and the board surface flow channel connection hole Sb3 and then enters the board surface flow channel connection holes Sf4, Sb4 and Sb2 through the mode select switch flow channel S1 and reaches the regulating module. After adjustment of the vacuum value, vacuum is output from the fitting port (P2); a suction operation mode is established. At the same time, the change valve flow channel C1 of the valve plate (5-2-2) of the change valve (5-2) enables the valve channel holes Qf4 and Qf3 to communicate with each other, and a controlling circuit is connected with the atmosphere. The vacuum power in the diaphragm piston (5-1) communicates with the atmosphere and is then relieved through the holes Pf3, Pb3, Pb1, Pf1, Pf2, the first timer regulating needle valve T0, the valve channel holes Qb3, Qf3, Qf4, Qb4 and the third time regulating needle valve T2. The return spring (5-1-3) in the diaphragm piston (5-1) actuates the diaphragm piston (5-1) to return to its original position to allow the intermittent timer (5) to reset.

C) When the intermittent timer (5) returns to a critical position, the crank (5-2-4) loses its stability again under the action of the torsion spring (5-2-3), and the crank (5-2-4) actuates the change valve (5-2) to rotate rapidly and thereby forcing the change valve (5-2) to change its status. The paths return to their original status and a cycle is completed.

For intermittent operation mode of Instant on the valve plate (5-2-2) must be replaced and then the change valve flow channels C1, C2, C3 are changed. The suction operation starts first and then the suction operation is closed by the change valve (5-2). The operation process of the principle of the intermittent operation mode of "instant on" is similar to the intermittent operation mode of "instant off" (see FIGS. 12, 13, 14, 15).

What is claimed is:

1. A combination suction regulator for medical use which comprises a cover, a vacuum gauge, a regulating module, an integrated flow channel module having a plurality of board surface flow channels, an intermittent timer, a mode select switch, a vacuum relief and an air buffer, wherein:
   A. the air buffer is disposed inside the cover and integrally formed as a whole with the integrated flow channel module, there are two air holes disposed on a left and on a right side of a bottom part of the air buffer for communicating with the board surface flow channels that are susceptible to interference in the integrated flow channel module;
   B. a flow channel board and a bottom board are coupled with each other to form the integrated flow channel module; the bottom board has a probe/adapter port at a middle part thereof which connects with an input vacuum source via a threaded connecting inlet, and three timer regulating needle valves on a board surface thereof for communicating with the corresponding board surface flow channels and adjusting the intermittent timer on and off; the flow channel board has a front side and a back side; the front side of the flow channel board has a pole at an upper end thereof for installing the mode select switch, and four to six board surface flow channel connection holes for communicating with the board surface flow channels on the flow channel board; in a middle part of the front side of the flow channel board, a metal pole, a timer channel hole and a valve seat of a change valve are disposed which are all connected to the intermittent timer; in a lower part of the front side of the flow channel board, a sleeve seat for installing the regulating module is disposed, which has mouths communicating with the board surface flow channels; and a threaded fitting port at a bottom part of the flow channel board forms an outlet of the suction regulator;
   C. the intermittent timer comprises a diaphragm piston disposed on one side and the change valve disposed on another side of the middle part of the front side of the flow channel board; the diaphragm piston comprises a body, a diaphragm, a return spring and piston rod; the change valve comprises a connecting rod, a crank and a torsion spring, a valve plate and the valve seat disposed in the middle part of the front side of the flow channel board; the diaphragm piston connects to and controls the change valve through the piston rod.

2. The combination suction regulator for medical use as in claim 1, wherein the front side of the flow channel board has six board surface flow channel connection holes Sf1-Sf6 at the upper end thereof, and the back side of the flow channel board has six corresponding board surface flow channel connection holes Sb1-Sb6.

3. The combination suction regulator for medical use as in claim 1, wherein one side of the mode select switch has mode select switch flow channels S1, S2, which form a mode selector with the board surface flow channel connection holes Sf1-Sf6 of the flow channel board.

4. The combination suction regulator for medical use as in claim 1, wherein the valve seat of the change valve has six valve channel holes Qf1-Qf6 in the middle part of the front side of the flow channel board and six corresponding valve channel holes Qb1-Qb6 on the back side of the flow channel board.

5. The combination suction regulator for medical use as in claim 1, wherein the valve plate of the change valve has change valve flow channels C1, C2, C3 which form the change valve with the six valve channel holes Qf1-Qf6 on the valve seat.

6. The combination suction regulator for medical use as in claim 1, wherein three timer regulating needle valves (T0, T1, T2) are on a back of the integrated flow channel module and used for communicating with the corresponding board surface flow channels to adjust time of the intermittent timer.

* * * * *